US00PP13165P2

(12) United States Plant Patent

Windham et al.

(10) Patent No.: US PP13,165 P2

(45) Date of Patent: Nov. 5, 2002

(54) DOGWOOD TREE NAMED 'KAREN'S APPALACHIAN BLUSH'

(75) Inventors: Mark T. Windham; Robert N. Trigiano; Willard T. Witte, all of Knoxville, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/654,765

(22) Filed: Sep. 5, 2000

Related U.S. Application Data

(60) Provisional application No. 60/210,603, filed on Jun. 9, 2000.

(51) Int. Cl.[7] ..... A01H 5/00

(52) U.S. Cl. ..... Plt./220

(58) Field of Search ..... Plt./220, 216

(56) References Cited

U.S. PATENT DOCUMENTS

| | | | |
|---|---|---|---|
| 8,500 | A | 12/1851 | Smith |
| 10,166 | A | 12/1853 | Nicholson |
| 10,423 | A | 6/1854 | Stanley |
| 11,654 | A | 11/1854 | Asaka |
| 2002/0035742 | A1 | 3/2002 | Windham et al. |

OTHER PUBLICATIONS

Windham, M.T., et al.; "Reactions of Cornus Species to Powdery Mildrew," SNA Research Confrerence, vol. 42, pp. 227–229 (42$^{nd}$ Annual Report, 1997).

Triginao, R.N., et al.; "Three New Cultivars of Flowering Dogwood Resistant to Powdery Mildew", *HortScience*, vol. 35(3), p. 490 (Jun. 2000).

Gary, L.B., "Appalachian Spring: New UT Cultivar is First to Resist Deadly Dogwood Disease,"*UT Agriculture Magazine* (Spring 1999).

Caetano–Anolles, G., et al., "DNA amplification fingerprinting and marker screening for pseudo–testcross mapping of flowering dogwood (*Cornus florida L.*)", *Euphytica*, 1999, 106:209–222; Pub: Kluwer Academic Publishers, Netherlands.

Gary, L.B., "Appalachian Spring: New UT Cutivar is First to Resist Deadline Dogwood Disease,"*UT Ag. Magazine*, Spring 1999, XP–002194700, Pub: Univ. of Tenn. Online.

Hagan, A.K., et al., "Susceptibility of Cultivars of Several Dogwood Taxa to Powdery Mildew and Spot Anthracnose", *J. Environ. Hort.*, 1998, 16(3):147–151, Pub: unknown.

Hanson, S., "Dogwood: Current and Future Research", 2000, XP–002194703 [online].

Hollins, S.J., et al., "Breeding Disease Resistant Flowering Dogwood (*Cornus florida*)", *SNA Research Conference*, 1999, 44:359–361 [online].

Ragland, C., "Dogwood Tree", *Dogwood, Microsoft® Encarta® Online Encylopedia*2000, XP–002194704, Pub. Microsoft Corporation.

Trigiano, R.N., et al., "Teaching Methods: Laboratory Exercises on DNA Amplification Fingerprinting for Evaluating the Molecular Diversity of Horticultural Species,"*Hor Technology*, 1998, 8(3):413–23, XP–001064538, Pub: Unknown.

Trigiano, R.N., et al., "Three New Cultivars of Flowering Dogwood Resistant to Powdery Mildew,"*Hort. Science*, 2000, 35(3):490, #549, XP–001064539, Pub: Unknown.

Unknown, "Powdery Mildew of Flowering Dogwood", 2000, XP–002194701 [online], Pub: The University of Tennessee Dogwood Research Group.

Windham, M.T., et al., "Are'Barton'and 'Cloud 9' the Same Cultivar of *Cornus florida L.* ?", *J. Environ. Hort.*, 1998, 16(3):163–166, XP–001064563, Pub: unknown.

Windham, M.T., et al., "Development of Flowering Dogwood Cultivars Resistant to Powdery Mildew", *Tenth Conference of Metropolitan Tree Improvement Alliance (Sep.–Oct.* 1998), XP–002194702 [online].

Windham, M.T., et al., "Naturally Occuring Resistance to Powdery Mildew in Seedlings of *Cornus florida*", *J. Envrion. Hort.*, 1998, 16(3):173–175, XP–001064535, Pub: unknown.

Windham, M.T., et al., "New Dogwood Cultivars Resistant to Powdery Mildew", *SNA Research Conference*, 2000, 45:204–205, XP–002194698 [online].

*Primary Examiner*—Bruce R. Campell

*Assistant Examiner*—June Hwu

(74) *Attorney, Agent, or Firm*—Saliwanchik, Lloyd & Saliwanchik

(57) ABSTRACT

A new and distinct cultivar of Dogwood tree, *Cornus florida*, named 'Karen's Appalachian Blush', is provided. This cultivar is characterized by resistance to powdery mildew which is superior to any other white flowering dogwood.

4 Drawing Sheets

1

CROSS-REFERENCE TO A RELATED APPLICATION

This application claims the benefit of U.S. Provisional Application No. 60/210,603, filed Jun. 9, 2000.

BACKGROUND OF THE INVENTION

The present invention relates to a new and distinct cultivar of flowering dogwood which is resistant to powdery mildew. This dogwood is botanically known as *Cornus florida* and hereinafter is referred to by the cultivar name 'Karen's Appalachian Blush'.

2

This new dogwood cultivar was discovered in a field planting of approximately 1,100,00 *Cornus florida* seeds in Decherd, Tenn. in 1995. 'Karen's Appalachian Blush' is a white flowering dogwood which, to the knowledge of the inventors, is superior to any other white flowering dogwood with respect to powdery mildew resistance. Asexual reproduction of 'Karen's Appalachian Blush' by terminal cuttings harvested at the Tennessee Agricultural Experiment Station in Knoxville, Tenn. has shown that the unique features of this new dogwood cultivar are stable and reproduced true to type in successive generations.

BRIEF DESCRIPTION OF THE DRAWINGS

FIG. 1. Photograph of a typical flower specimen of 'Karen's Appalachian Blush'. This photograph is a closeup view of a typical flower of this cultivar.

FIG. 2. A similarity index for various dogwoods.

FIG. 3. Cluster analysis of various dogwoods.

FIG. 4. Principal coordinate analysis of the relationships between the dogwoods.

Flower colors in the photograph may differ from the actual colors due to light reflectance.

DETAILED DESCRIPTION OF THE NEW VARIETY

The parental lineage of this cultivar is unknown. 'Karen's Appalachian Blush' is a white flowering dogwood cultivar isolated from a field planting of approximately 1,100,000 *Cornus florida* seeds in Decherd, Tenn. Seeds were bulked from collections of wild and landscape trees from Tennesee, North Carolina, Alabama, and Georgia. This cultivar may be reproduced asexually by rooting cuttings and by grafting.

'Karen's Appalachian Blush' has white bracts which develop a pink blush along the margins. The bracts are long and floppy, do not overlap, and are delicate in appearance. Upper pairs of bracts average about 13.3 cm long by about 8.8 cm wide in size (n=30). Clefts at the ends of the bracts are pointed or flat and have little pigmentation. Flower petals are yellow and flowers average 20 per inflorescence (n=15).

'Karen's Appalachian Blush' is, to the knowledge of the inventors, superior in resistance to powdery mildew to any other white flowering dogwood cultivar. This cultivar has been tested for three (3) years. Test plants were exposed to powdery mildew and assessed for resistance to powdery mildew. Mildew scores for 'Karen's Appalachian Blush', control plants, and 'Cherokee Brave' were obtained using the following scale: 0=healthy; 1=≦2% of foliage with signs or symptoms of powdery mildew, 2=≦10% of foliage with signs or symptoms of powdery mildew; 3=≦25% of foliage with signs or symptoms of powdery mildew; 4=≦50% of foliage with signs or symptoms of powdery mildew; 5=≦75% of foliage with signs or symptoms of powdery mildew; 6=≦100% of foliage with signs or symptoms of powdery mildew. Table 1 presents the data obtained over the last three (3) years.

| Year | 'Karen's Appalachian Blush' | Control Score[1] | 'Cherokee Brave'[2] |
|---|---|---|---|
| 1996 | 0.0 | 5.8(a) | — |
| 1997 | 0.0 | 6.0(b) | 2.3 |
| 1998 | 1.0 | 4.8(c) | 2.1 |

[1]Control plants were (a) *Cornus florida* seedlings, (b) 'Cherokee Sunset', or (c) 'Cherokee Daybreak' that were of similar age and size.
[2]'Cherokee Brave' is a pink flowering dogwood cultivar which is the only cultivar known to the inventors to possess resistance to powdery mildew.

DNA amplification fingerprinting was used to type 'Jean's Appalachian Snow', 'Kay's Appalachian Mist', and 'Karen's Appalachian Blush'. The methodology followed that of Trigiano and Caetano-Anollés (HortTechnology, 8:413–423 [1998]). Data, obtained from 235 loci generated from genomic DNA using seven (7) arbitrary octomeric primers, was used to compare the powdery mildew resistant dogwoods of the subject application to other dogwoods (including powdery mildew resistant lines and cultivars commonly found in nurseries). The sequences of the primers were as follows: 1) GAGGCCTGT, 2) GTTACGCC, 3) CCTGTGAG, 4) GTAACGCC, 5) GACGTAGG, 6) GATCGCAG, And 7) GTATCGCC. DNA amplification fingerprinting analysis as well as the cluster and principal coordinate analysis were completed using the NTSYS PROGRAM, pc version, 2.2 (Exeter Software, 100 N. Country Road, Sedtauket, N.Y. 11733). A similarity index is provided in FIG. 2. FIG. 3 depicts the resulting cluster analysis. FIG. 4 depicts the principal coordinate analysis of the relationships between the dogwoods.

The abbreviations found in the Figures are as follows: AS='Appalachian Spring', KAM='Kay's Appalachian Mist', JAS='Jean's Appalachian Snow', C9='Cloud Nine', KAB='Karen's Appalachian Blush', CP='Cherokee Princess', SPR='Springtime' and CB='Cherokee Brave'. All are white bract dogwoods except, CB, which is red.

DETAILED BOTANICAL DESCRIPTION

The following observations, measurements, and comparisons describe this cultivar grown in Knoxville, Tenn. under container nursery conditions which approximate commercial production conditions. Dogwoods used for this description were about five (5) years old and were grown in twenty-five (25) gallon containers. Plant hardiness is expected to be zones 5–9.

The following description uses color references to The Royal Horticultural Society Colour Chart, except where general terms of ordinary dictionary significance are used. All color ratings were on adaxial surfaces. Color ratings for abaxial surfaces were not obtained because reflected/refracted light, due to the density of pubescence on abaxial surfaces, made accurate color determinations difficult or impossible. Measurements are provided as a range with the middle value providing the average (lower limit<average value<upper limit).

Botanical classification: *Cornus florida*, cultivar 'Karen's Appalachian Blush'.

Parentage: Unknown.

Propagation:

*Type.*—Terminal softwood cuttings.

*Time to initiate roots (in June).*—About 3–4 weeks at about 25–30° C.

*Rooting habit.*—Profuse from base of cutting.

*Rooting hormone.*—5,000–10,000 ppm; five (5) second quick dip of DIP 'N' GROW (1% IBA, 0.5% NAA) (Dip 'N' Grow, Inc., Clackamas, Oreg.).

*Intermittent mist.*—Six (6) seconds every six (6) minutes.

*Light.*—30–50% shade cloth over propagation bench.

*Media.*—Peat-perlite.

Plant description:

*Plant form and growth habit.*—Perennial deciduous tree, mostly upright with horizontal branching.

*Plant size.*—A five (5) year old tree will attain a height of about 240 cm and a width of about 110 cm.

*Vigor.*—Similar to other *Cornus florida* cultivars.

*Branching habit.*—Moderate, branch crotch angles of about 20–40° to main trunk.

*Main stem/trunk description.*—Diameter: About 3.3 cm; bark texture: smooth; bark color: gray 201C.

*Lateral branch description.*—Branch angle of about 45° with a range of 40–48°.

Foliage description:

*Arrangement.*—Simple, opposite; leaves mostly crowded towards branch apices.

*Leaf blade length (cm).*—About 9.9<11.2<12.5 (n=5).

*Leaf blade width (cm).*—6.0<7.5<8.8 (n=5).

*Petiole length (cm).*—1.1<1.4<1.7 (n=5).

*Petiole diameter (mm).*—About 1.1<1.3<1.45 (n=5).

*Shape.*—Broadly ovate.

*Apex.*—Acuminate, leaf tips mostly flat.

*Base.*—Acute to cuneate, about 10% unequal.

*Margin.*—Entire, slightly undulate.

*Texture.*—Upper surface: Nearly glabrous. Lower surface: leaf hairs profuse on veins and vein axils ($\mu$) — 16<25<36.

*Color.*—Yellow green 146C.

*Leaf vein arrangement.*—Six (6) pairs, mostly opposite. Petiole reflexed 80°–90° from plane of leaf blade.

*Bipolar trichomes.*—Upper surface — low density ($\mu$) — 6<7.2<10 Lower surface ($\mu$) — 6<9.8<14.

Flower description:

*Fragrance.*—None observed.

*Flower bud size.*—Width: 6.4 mm (widest diameter). Length: 5 mm (base to tip).

Shape of involucral bracts.—Obovate/pandurate.

Apex shape of involucral bracts.—Mucronate.

Base shape of involucral bracts.—Cuneate.

*Number of bracts.* 4 (in two pairs).

*Natural flowering season.*—1999: about 15 days (April 10 through April 25). 2000: about 16 days (April 5 though April 21). 2001: about 15 days (April 12 through April 27).

*Inflorescence arrangement.*—Bracts long and floppy; do not overlap.

*Inflorescence diameter.*—About 27 cm wide.

*Bract dimensions.*—Upper bracts about 13.3 cm long by about 8.8 cm wide. Inflorescence is 5.9 mm wide; anther length is 1.2 mm. Floral development is asynchronous among inflorescence.

*Color (abaxial and adaxial surfaces).*—White (155D) bracts develop a pink blush (73B) suffused along the margin. Clefts are pointed or flat with little red-purple (60A) pigmentation.

*Sepals.*—Typically 4.

*Stamens.*—Typically 4.

*Pistil.*—Typically 1.

*Flower number.*—20.

*Petal color (abaxial and adaxial surfaces).*—Yellow green 151B.

*Ovary.*—Bilocular with each locule having 1 ovule.

Fruit description:

*Berry type.*—Drupe (about 14 mm by 7 mm) aggregated in one mass.

*Color.*—10R(6/10) using Munsell Color Chart for Plant Tissues (Munsell Color, Baltimore, Md. 21218).

Disease resistance: This cultivar demonstrated outstandng resistance to powdery mildew superior to that of any other white flowering dogwood cultivar known to the inventors. No susceptibility to other diseases or arthropod pests was observed.

What is claimed is:

1. A new and distinct cultivar of Dogwood tree, *Cornus florida*, named 'Karen's Appalachian Blush', as illustrated and described.

* * * * *

| | AS | KAM | JAS | C9 | KAB | CP | SPR | CB |
|---|---|---|---|---|---|---|---|---|
| AS | 1.00 | | | | | | | |
| KAM | 0.80 | 1.00 | | | | | | |
| JAS | 0.76 | 0.76 | 1.00 | | | | | |
| C9 | 0.75 | 0.70 | 0.77 | 1.00 | | | | |
| KAB | 0.79 | 0.79 | 0.78 | 0.75 | 1.00 | | | |
| CP | 0.78 | 0.84 | 0.82 | 0.78 | 0.85 | 1.00 | | |
| SPR | 0.78 | 0.82 | 0.76 | 0.77 | 0.82 | 0.86 | 1.00 | |
| CB | 0.79 | 0.77 | 0.73 | 0.72 | 0.78 | 0.79 | 0.82 | 1.00 |

LEGEND: AS = 'Appalachian Spring', KAM = 'Kay's Appalachian Mist', JAS = 'Jean's Appalachian Snow', C9 = 'Cloud Nine', KAB = "Karen's Appalachian Blush', CP = 'Cherokee Princess', SPR = ' Springtime' and CB = 'Cherokee Brave'. All are white bract dogwoods except CB, which is red.

FIG. 2